US00PP31669P2

(12) United States Plant Patent
Heimovaara

(10) Patent No.: US PP31,669 P2
(45) Date of Patent: Apr. 14, 2020

(54) ***CHRYSANTHEMUM* PLANT NAMED 'ZANMUDOVE YELLOW'**

(50) Latin Name: ***Chrysanthemum* x *morifolium* Ramat.**
Varietal Denomination: Zanmudove Yellow

(71) Applicant: Van Zanten Breeding BV, Aalsmeer (NL)

(72) Inventor: Sjoukje Heimovaara, Valkenburg (NL)

(73) Assignee: VAN ZANTEN BREEDING BV (NL)

( * ) Notice: Subject to any disclaimer, the term of this patent is extended or adjusted under 35 U.S.C. 154(b) by 0 days.

(21) Appl. No.: 16/350,568

(22) Filed: Dec. 4, 2018

(51) Int. Cl.
*A01H 5/02* (2018.01)
*A01H 6/14* (2018.01)

(52) U.S. Cl.
USPC ..... Plt./289

(58) Field of Classification Search
USPC ..... Plt./289
See application file for complete search history.

*Primary Examiner* — Susan McCormick Ewoldt
(74) *Attorney, Agent, or Firm* — Steptoe & Johnson LLP

(57) ABSTRACT

A *Chrysanthemum* plant named 'Zanmudove Yellow' characterized by its medium sized blooms with light yellow ray florets and prolific branching; natural season flowering date October 1 (week 40); blooming for a period of 5 weeks.

2 Drawing Sheets

Botanical designation: *Chrysanthemum* x *morifolium* Ramat.

Cultivar denomination: "Zanmudove Yellow".

RELATED CULTIVARS

The new plant is a flower color mutant of 'Zanmudove' (U.S. Plant Pat. No. 24,618)

BACKGROUND OF THE INVENTION

The present invention relates to a new and distinct cultivar of *Chrysanthemum* plant, botanically known as *Chrysanthemum* x *morifolium* Ramat., commercially known as a garden mum, and hereinafter referred to by the cultivar denomination 'Zanmudove Yellow'. 'Zanmudove Yellow' is a product of a breeding and selection program which had the objective of finding flower color mutants from existing parent plants. The new plant comprises a whole plant mutant of the parent *Chrysanthemum* named 'Zanmudove'. Plants from the new cultivar 'Zanmudove Yellow' differ from plants of the parent in the color of the ray-florets. The ray-florets of the parent are white, while those of the new plant are yellow.

The new plant was discovered as a natural flower color mutant in October 2016 by Sjoukje Heimovaara. The first act of asexual reproduction of 'Zanmudove Yellow' was accomplished when after planting of the new variety as a motherplant in November 2016, vegetative cuttings from this motherplant were taken and propagated further in Rijsenhout, the Netherlands. In summer, about 6-8 days are needed to initiate roots in cuttings of the new cultivar, after another 5 days rooted plants are formed. The new cultivar has been found to retain its distinctive characteristics through successive propagations.

BRIEF DESCRIPTION OF THE DRAWINGS

The present invention of a new and distinct variety of *Chrysanthemum* (of about 21 weeks) is shown in the accompanying drawings, the color being as nearly true as possible with color photographs of this type.

DESCRIPTION OF THE INVENTION

Figure 1:
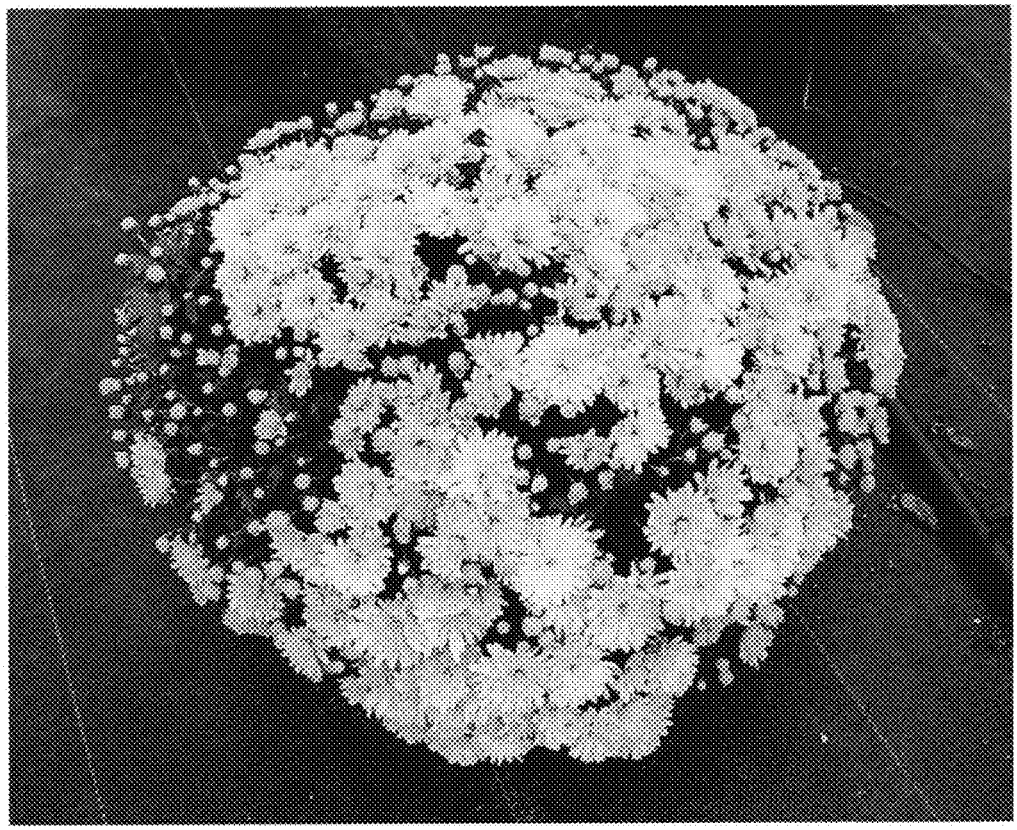
FIG. 1 shows a plant of the new cultivar in full bloom.
Figure 2:
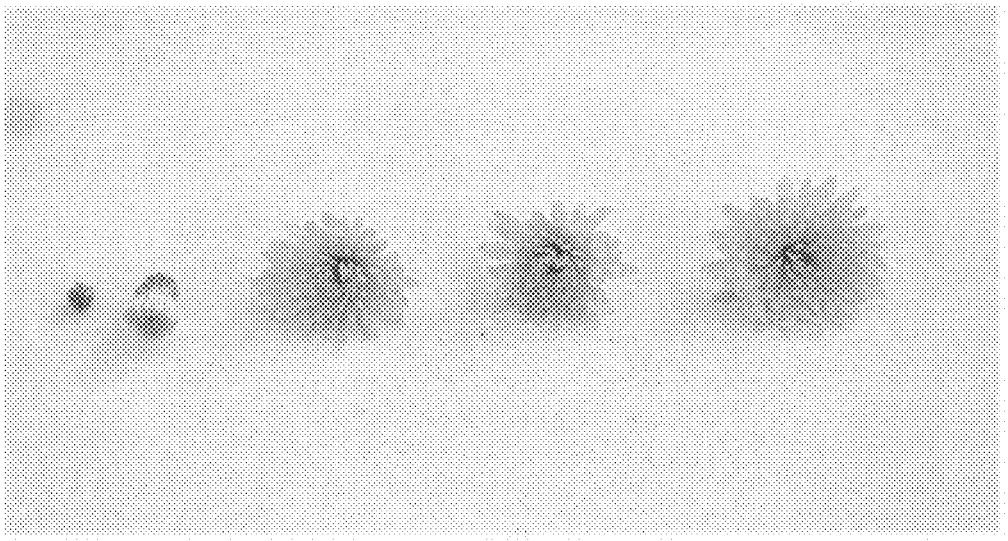
FIG. 2 shows the various stages of blooms of the new cultivar.
Figure 3:
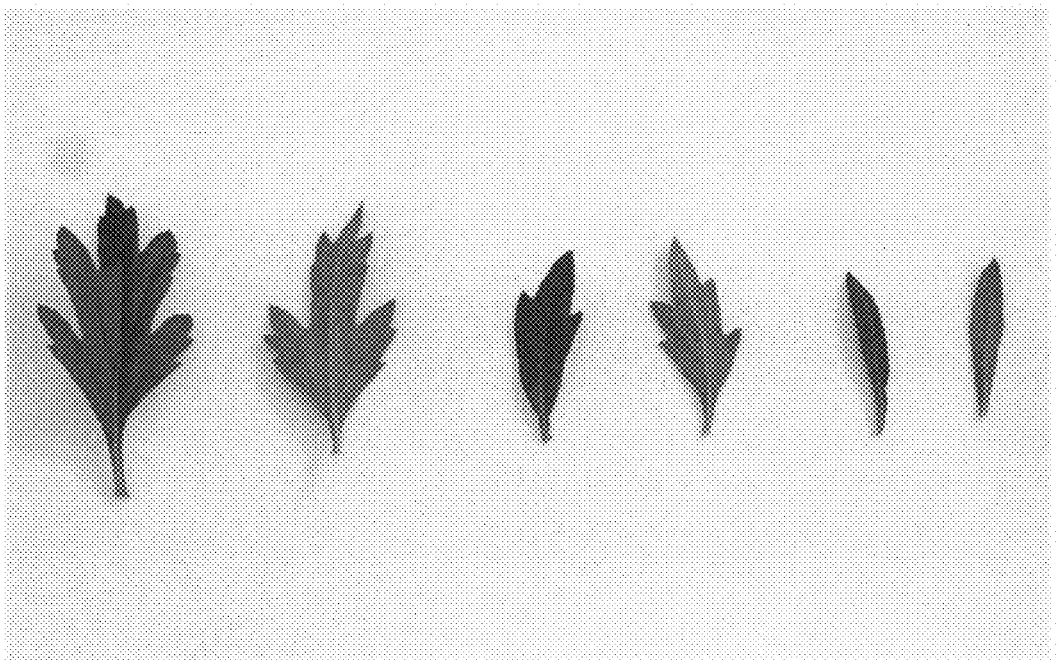
FIG. 3 shows the various stages of foliage of the new cultivar.

The observations and measurements were gathered from plants in the period of 19 to 25 weeks of age grown outdoors in Rijsenhout, the Netherlands, under natural day length and temperature and planted in week 21 in 2018. The natural blooming date of this crop was October 1 (week 40). The average height of the plants was 28 cm. No growth retardants were used. No tests were done on disease or insect resistance or susceptibility. No tests were done on cold or drought resistance. This new variety produces medium sized blooms with light yellow ray florets blooming for a period of five weeks. From the cultivars known to the inventor the most similar existing cultivar in comparison to 'Zanmudove Yellow' is 'Zanmuday' (U.S. Plant Pat. No. 24,670). When 'Zanmuday'and 'Zanmudove Yellow' are compared the following differences are noticed: Ray-florets of Zanmuday' are white, while those of 'Zamudove Yellow' are light yellow.

The following is a description of the plant and characteristics that distinguish 'Zanmudove Yellow' as a new and distinct variety.

The color designations are taken from the plant itself. Accordingly, any discrepancies between the color designations and the colors depicted in the photographs are due to photographic tolerances. The color chart used in this description is: The Royal Horticultural Society Colour chart, edition 2001.

Botanical Description of *Chrysanthemum* x *morifolium* Ramat. 'Zanmudove Yellow'

Bud:
*Size*.—Small; cross-section 6 mm, height 4 mm.
*Shape*.—Round.
*Texture*.—Pubescent.
*Outside color*.—Greyed-green 191A.

Phyllaries:
*Number*.—24, arranged in 3 rows.
*Shape*.—Elliptic.
*Apex*.—Acute.
*Base*.—Truncate.
*Margin*.—Entire.
*Color*.—Upper side: Green 138A. Lower side: Green 135B.
*Length and width*.—3-5 mm; 1.5 mm.
*Texture*.—Pubescent.

Inflorescences:
*Type*.—Double.
*Height*.—1.5 cm.
*Diameter*.—4-5 cm.
*Peduncle length*.—6-7 cm.
*Peduncle color*.—Greyed-green 194B.
*Peduncle diameter*.—1-1.5 mm.
*Peduncle texture*.—Pubescent.
*Peduncle strength*.—Not strong.
*Number per branch*.—About 6-8 inflorescences.
*Duration of flowering*.—5 weeks.
*Seeds*.—Produced in small quantities, ovate, Greyed-brown 199A, length 1.5 mm, diameter 0.5 mm; texture: rough with ribs.
*Fragrance*.—Faint *Chrysanthemum* odor.

Color inflorescences:
*Center of inflorescence*.—Immature stage: Yellow 7A; Mature stage: Yellow 13A.
*Color of upper side of ray florets*.—Yellow 8B.
*Color of lower side of ray florets*.—Yellow 8D.
*Tonality from distance*.—A garden mum with yellow blooms.
*Color of ray florets after aging of the plant*.—Yellow 5D.

Ray florets:
*Number of types*.—One.
*Type*.—Ligulate.
*Texture*.—Upper and lower side smooth.
*Number*.—180-190.
*Shape*.—Elliptic.
*Apex*.—Dentate to Rounded.
*Base*.—Attenuate.
*Cross-section*.—Flat.
*Longitudinal axis*.—Straight.
*Length of corolla tube*.—3 mm.
*Diameter corolla tube*.—1 mm.
*Ray floret margin*.—Entire.
*Ray floret length*.—1.4-2.3 cm.
*Ray-floret width*.—2-5 mm.
*Ratio length/width*.—High.

Disc florets:
*Disc diameter*.—2 mm.
*Number of disc florets*.—5-10.
*Shape*.—Funnel shaped.
*Color*.—Yellow-green 145C at base to Green Yellow 11D at apex.
*Length*.—4 mm.
*Diameter*.—0.8 mm.

Receptacle:
*Color*.—Yellow-green 145D.
*Shape*.—Domed raised.
*Height*.—3 mm.
*Diameter*.—3 mm.

Reproductive organs:
*Androecium*.—Present on only disc florets.
*Stamen length*.—3 mm.
*Stamen color*.—Yellow-green 144A.
*Anther color*.—Yellow 2A.
*Pollen*.—Present in a moderate amount.
*Pollen color*.—Yellow 13A.
*Gynoecium*.—Present on both ray and disc florets.
*Style color*.—Yellow-green 154C.
*Style length*.—4 mm.
*Stigma color*.—Yellow 7A.
*Stigma width*.—1 mm.
*Ovary*.—Enclosed in calyx.
*Ovary color*.—Yellow-green 149D.

Plant:
*Type*.—Bushy.
*Growth habit*.—Spherical shape.
*Growth rate*.—Medium.
*Height*.—28 cm.
*Width*.—45-50 cm.
*Stem color*.—Greyed-brown 199A.
*Stem strength*.—Medium strength.
*Stem brittleness*.—Moderately brittle.
*Stem anthocyanin coloration*.—Not observed.
*Internode length*.—2 cm.
*Length of lateral branch*.—From top to bottom 18-20 cm.
*Lateral branch color*.—Green 138B.
*Lateral branch, attachment*.—Weak.
*Lateral branch diameter*.—2-2.5 mm.
*Lateral branch texture*.—Pubescent with ribs.
*Branching* (*average number of lateral branches*).—Prolific with 9 breaks after pinching.
*Natural season blooming date*.—October 1 (week 40) in Rijsenhout, the Netherlands.
*Root habits*.—Fine, freely branching.
*Root color*.—White 155D.
*Rooting time*.—6-8 days.
*Formation rooted plants*.—12-14 days.

Foliage:
*Leaf glossiness*.—Upperside: Very weak. Lower side: Very weak.
*Leaf color*.—Upper side: Green 137A. Lower side: Green 137B.
*Color midvein*.—Upper side: Yellow-green 147D. Lower side: Yellow-green 148D.
*Size*.—Small; length 2.6-5.5 cm, width 0.5-2.5 cm.
*Quantity* (*number per lateral branches*).—25.
*Shape*.—Elliptic.
*Texture upper side*.—Sparsely pubescent.
*Texture under side*.—Pubescent.
*Venation arrangement*.—Pinnate.
*Shape of margin*.—Serrated to Entire.
*Shape of base of sinus between lateral lobes*.—Rounded.

*Margin of sinus between lateral lobes*.—Diverging.

*Shape of base*.—Attenuate.

*Apex*.—Mucronulate.

*Petiole attitude*.—Moderately upwards.

*Petiole length*.—0.5-1 cm.

*Petiole diameter*.—1-1.5 mm.

*Petiole color*.—Yellow-green 147D.

*Stipules*.—Small.

TABLE 1

Differences with the comparison variety, when grown under identical conditions

| Characteristic | 'Zanmuday' | 'Zanmudove Yellow' |
|---|---|---|
| Natural season blooming date | Week 41 | Week 40 |
| Color upperside ray-florets | Yellow 12B | Yellow 8B |

I claim:

1. A new and distinct *Chrysanthemum* plant named 'Zanmudove Yellow' as described and illustrated.

* * * * *